United States Patent [19]

Laub

[11] Patent Number: 4,808,163
[45] Date of Patent: Feb. 28, 1989

[54] PERCUTANEOUS VENOUS CANNULA FOR CARDIOPULMONARY BYPASS

[76] Inventor: Glenn W. Laub, 16 Cameron Ct., Princeton, N.J. 08540

[21] Appl. No.: 79,118

[22] Filed: Jul. 29, 1987

[51] Int. Cl.$^4$ ............................................. A61M 29/00
[52] U.S. Cl. .................................. 604/105; 604/282; 604/53; 128/345
[58] Field of Search ................. 604/105, 4, 280–282, 604/51, 52, 53, 93, 104, 106–107; 128/341–345

[56] References Cited

U.S. PATENT DOCUMENTS

| | | | |
|---|---|---|---|
| 3,490,457 | 1/1970 | Petersen | 604/105 |
| 3,938,530 | 2/1976 | Santomieri | 604/105 |
| 3,946,741 | 3/1976 | Adair | 604/105 |
| 4,660,571 | 4/1987 | Hess et al. | 604/105 |
| 4,699,611 | 10/1987 | Bowden | 604/105 |

Primary Examiner—C. Fred Rosenbaum
Assistant Examiner—Gene B. Kartchner
Attorney, Agent, or Firm—Reed Smith Shaw & McClay

[57] ABSTRACT

A cardiovascular catheter for use particularly in situations requiring varying forms of cardiopulmonary bypass. The catheter which can be introduced percutaneously has an expandable section in proximity to drainage inlets. In one form of the invention the catheter is introduced percutaneously with the expansion means collapsed after the cannula has been introduced percutaneously through the vein into the right atrium the expansion means is employed to prevent the atrium from collapsing around and possibly impeding flow through the cannula, for instance during percutaneous initiation of cardiopulmonary bypass or other venous drainage application.

8 Claims, 1 Drawing Sheet

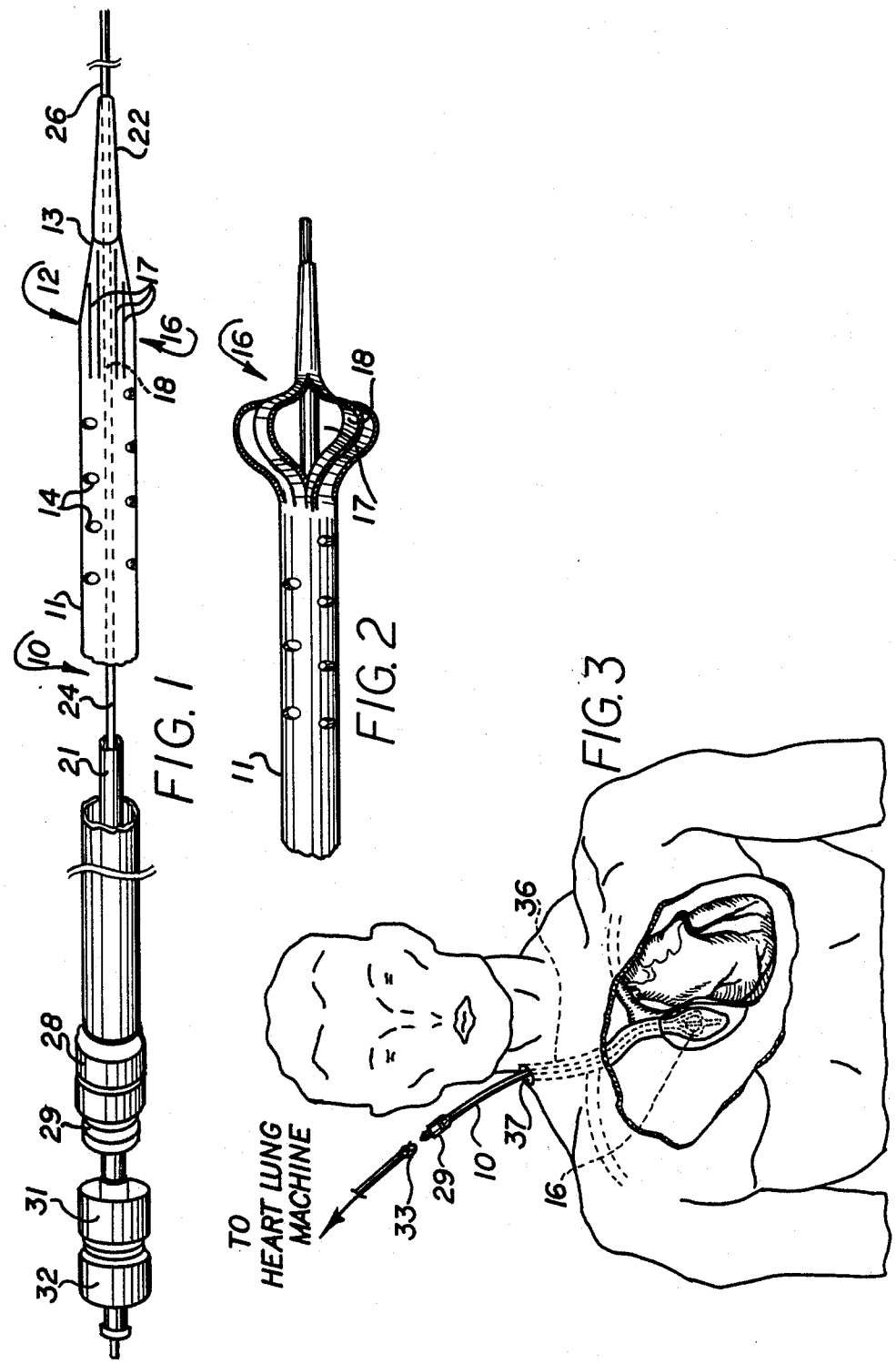

4,808,163

PERCUTANEOUS VENOUS CANNULA FOR CARDIOPULMONARY BYPASS

FIELD OF THE INVENTION

The present invention relates to a cannula for percutaneous initiation of cardiopulmonary bypass and, in particular, a means for and method of percutaneous cardiopulmonary bypass. The invention may also be used with extracorporeal membrane oxygenation as well as other procedures where venous drainage may be necessary.

BACKGROUND OF THE INVENTION

Traditionally, the establishment of cardiopulmonary bypass for circulating blood into a heart lung machine has required major surgical intervention. Venous cannula and cardiovascular catheters are normally utilized in draining the venous blood into the heart lung machine, e.g., U.S. Pat. Nos. 3,903,895 and 4,248,224. Venous cannula must be located in or near the central venous circulation. To obtain sufficient venous return to achieve full cardiopulmonary bypass a major operation is required to place the cannula directly into the right atrium. This is normally done by performing a median sternotomy or thoracotomy to surgically expose the right atrium. Arterial return is normally through the aorta or femoral artery. Alternatively, the venous cannula can be introduced into surgically exposed femoral or jugular veins.[1]

[1] Percutaneous cardiopulmonary bypass and innovations in clinical counterpulsation; S. J. Phillips, pp. 297-317, Critical Care Clinics, Vol. 2, No. 2, April, 1986.

Because the traditional establishment of full cardiopulmonary bypass requires major surgical intervention, partial supportive cardiopulmonary bypass through surgical exposure of the femoral artery and veins has been an accepted technique. However, this technique has not achieved widespread popularity for emergency applications, because it still requires a skilled surgical team and is extremely difficult to perform in environments in which a patient is undergoing cardiopulmonary resuscitation. In such circumstances, percutaneous cannulation of the femoral artery and both femoral veins has been utilized.[2] Notwithstanding the advantages provided by such percutaneous cannulation, full bypass through this method has not been achieved. Moreover, percutaneous cannulation of the jugular veins has not been performed.

[2] See, Percutaneous Initiation of Cardiopulmonary Bypass, Phillips, et al., The Annals of Thoracic Surgery, Vol. 36, No. 2, August, 1983, pp. 223-225.

Accordingly, it is an object of the present invention to provide a means and methods for percutaneous cannulation for initiation of full cardiopulmonary bypass without the need for a skilled surgical environment. It is a further object of the present invention to provide a venous cannula which can be percutaneously placed within the jugular veins as well as the femoral veins to achieve full bypass circulation as well as partial bypass, extracorporeal membrane oxygenation as well as other situations where venous drainage might be necessary.

SUMMARY OF THE INVENTION

Generally, the present invention provides a unique cannula having at its distal end a plurality of openings for the passage of blood. Also located at the distal end is an expansion means for dilating the walls of the vein, atrium, ventricle or other cavity after its insertion so as to space said walls from the openings receiving the blood. This expansion means prevents the walls of the vein, atrium or other surrounding vasculature from collapsing around and possibly impeding the flow of blood from the vascular space into the cannula. Inserted within and through the cannula is a stylet which extends the length thereof and protrudes through the distal end of the cannula.

At its distal end the stylet is tapered to facilitate percutaneous insertion thereof into the vein. A guidewire can be utilized which extends through the stylet opening. The guidewire is utilized to guide the cannula into the vein or vascular structure.

In practice a needle is inserted into the vein percutaneously, preferably after the use of local anesthesia, and the guidewire is introduced through the needle into the vein. After possibly nicking the skin with a scalpel and/or dilating the tissue with dilators the cannula and stylet are passed over the guidewire into the vascular structure. Once inserted, the stylet and guidewire are removed from the cannula. As the stylet is removed, the expansion means expands to prevent the vascular space from collapsing around the cannula to permit a full flow of blood to reach the openings at the distal ends of the cannula. By reason of the expansion means, dilation of the veins or atrium, full bypass of 4-5 liters per minute can be achieved.

The present invention provides a means and a method for achieving full cardiopulmonary bypass without the need for surgical intervention or specialized surgical procedures. The present invention is particularly useful in emergency or traumatic situations where cardiac surgical operating rooms are unavailable or where time or difficulty precludes the establishment of traditional cardiopulmonary bypass. Other advantages of the present invention will become apparent from a perusal of the following detailed description of the presently preferred embodiment taken in connection with accompanying drawings.

BRIEF DESCRIPTION OF THE DRAWINGS

FIG. 1 is a partial breakaway perspective view of the percutaneous venous cannula of the present invention;

FIG. 2 is a side elevation of the distal end of the cannula showing expansion of the expansion means; and FIG. 3 is a diagrammatic view of an inserted venous cannula in the right internal juggular vein.

PRESENTLY PREFERRED EMBODIMENT

Referring to FIG. 1, venous cannula 10 of the present invention preferably comprises an elongated tubular member 11 is made from a sterilizable flexible material such as preferably polyurethane. Tube 11 can have any desired length, but is generally around twentyfour inches long.

Positioned between opening 13 and openings 14 is expansion means 16. Expansion means 16 comprises a plurality of spaced-apart slits 17 which form the edges of ribs 18 (shown in FIG. 2). Expansion means 16 is formed by expanding ribs 18 and heat treating distal end 12 to provide a memory hysteresis such that the natural repose of cannula 10 is in the expanded mode shown in FIG. 2.

Cannula 10 also includes stylet 21 which extends therethrough and exits distal end 13. Preferably, the outer diameter of stylet 21 is slightly larger than distal opening 13 such that distal end 22 of stylet 21 engages the inner circumference of opening 13 as it extends therethrough. As stylet 21 extends through opening 13 it causes compression of expansion means 16 by forcing ribs 18 to lie within the surface geometry of cannula tube 11. That is, stylet 21 elongates expansion means 16 as it passes through opening 13. Further, stylet 21 preferably has a central lumen to allow the cannula 10, stylet 21 assembly, to be inserted over a guidewire if so desired.

Secured at the other end of tube 11 is connector 28 which includes threaded end portion 29 for receiving connector 31 attached to stylet 21. Adapter 33 connects cannula 10 to a heart lung machine (not shown) or the bypass device.

As diagrammatically shown in FIG. 3, cannula 10 is inserted in the right internal jugular vein 36 through percutaneous opening 37. The walls of the atrium are dialated by expanding expansion means 16 by retracting stylet 21. Expansion means 16 remains in its expanded mode until stylet 21 is reinserted.

The method for inserting cannula 10 into vein 36 includes locally anesthetizing the area to prepare for opening 37. A needle is inserted through the skin into vein 36. The guidewire 26 is inserted through the needle and advanced into vein 36. The needle is removed, the skin nicked in the area where the guidewire percutaneously transverses the skin to form opening 37. Cannula 10 with stylet assembly 21 is passed over guidewire 26 through opening 37 into vein 36. After positioned as shown in FIG. 3, stylet 21 and guidewire 26 are removed from cannula tube 11. The removal of stylet 21 permits expansion means 16 to expand and let the flow of blood to pass through openings 14 in tube 11. Cannula 10 is connected through adapter 33 to a heart lung machine.

While a presently preferred embodiment of the invention has been shown and described in particularity, it may be otherwise embodied within the scope of the appended claims.

What is claimed is:

1. A venous cannula for performing full or substantially full cardiopulmonary bypass comprising
   a. a cannula having an opening at its distal end and a plurality of openings positioned around and through the cannula at its distal portion;
   b. expansion means integrally formed adjacent the distal end of said cannula, said expansion means being adapted to dilate the walls of a vascular space and space said walls away from said openings, said expansion means having memory hysteresis, whereby said expansion means has a natural repose comprising an expanded orientation; and
   c. a stylet slidably positioned within said cannula and having a diameter slightly larger than said opening in the distal end of said cannula; said stylet having a tapered distal end adapted to extend through said opening in the distal end of said cannula whereby the degree of engagement of the stylet with the periphery of the opening at the distal end of said cannula controls the expansion and contraction of said expansion means.

2. A venous cannula as claimed in claim 1 wherein said distal end of said stylet terminates in a tapered edge for percutaneous initiation of said venous cannula into a blood vessel.

3. A venous cannula as claimed in claims 1 or 2 including a guidewire for insertion through an opening into a blood vessel, said guidewire being positioned through said stylet.

4. A venous cannula as claimed in claims 1 or 2, wherein said expansion means includes slits defining ribs formed from said cannula and biased to arcuately project from the surface of said cannula, said ribs being positionable into the surface plane of said cannula such that said slits of adjacent ribs substantially abut each other.

5. A method for the percutaneous initiation of full or substantially full cardiopulmonary bypass using the venous cannula set forth in claims 1 or 2, said method comprising the steps of
   a. positioning the stylet into a blood vessel percutaneously through the skin and said vessel wall, said stylet forcing said expansion means to compress;
   b. continuing said insertion into the vessel to position said cannula within the vessel;
   c. retracting said stylet so that said expansion means dilates said vessel wall to permit blood to flow through said openings; and
   d. connecting said cannula to a bypass line.

6. A method as set forth in claim 5, wherein said blood vessel is selected from the group consisting of femoral vein, jugular vein and subclavian vein.

7. A method as set forth in claim 6, wherein a guide means is first inserted into said blood vessel and said guide means is used to guide said cannula into said blood vessel.

8. A method as set forth in claim 7, wherein said guide means includes a guide wire, said guide wire being slidably received by said cannula, and said guide wire is removed from said cannula following positioning of said cannula within said vessel.

* * * * *